United States Patent [19]

Beatrice et al.

[11] Patent Number: 4,906,349

[45] Date of Patent: Mar. 6, 1990

[54] PROCESS FOR THE MANUFACTURE OF A MEASURING PROBE FOR A MEASURING HEAD TO DETECT THE OXYGEN ACTIVITY OF METAL MELTS AND A MEASURING PROBE MANUFACTURED BY SUCH A PROCESS

[75] Inventors: Pamela Beatrice, Shaker Heights; Herbert L. Johns, Madison, both of Ohio; Hans Leistner, Ingelheim, Fed. Rep. of Germany; James R. Wright, Bedford; Ronne Proch, Chagrin Falls, both of Ohio

[73] Assignee: Zircoa Incorporation, Solon, Ohio

[21] Appl. No.: 262,735

[22] Filed: Oct. 12, 1988

[51] Int. Cl.$^4$ .............................. G01N 27/58
[52] U.S. Cl. ...................... 204/422; 51/319; 134/42; 156/667
[58] Field of Search .............. 204/421, 422, 423; 156/667; 134/42; 51/319

[56] References Cited

U.S. PATENT DOCUMENTS

| | | | |
|---|---|---|---|
| 4,318,770 | 3/1982 | Chakupurakal | 156/637 |
| 4,327,122 | 4/1982 | Chakupurakal | 427/57 |
| 4,493,746 | 1/1985 | Reed | 156/644 |
| 4,575,410 | 3/1986 | Neti et al. | 204/422 |

FOREIGN PATENT DOCUMENTS 72021  6/1978  Japan ........................... 156/667

OTHER PUBLICATIONS

Stahl U., Eisen 95 (1974) No. 12, S,547,51.
Ferrotron, Ferrotron Elektronik GmbH, issue 1, (1982).

Primary Examiner—G. L. Kaplan
Attorney, Agent, or Firm—Wenderoth, Lind & Ponack

[57] ABSTRACT

A measuring probe for a measuring head to detect the oxygen activity of metal melts has a reference substance of known oxygen activity, which upon submersion into the metal melt is separated from the metal melt by means of a refractory solid electrolyte that conducts electrons reliably and conducts primarily oxygen at higher temperatures and which permits the measurement of the electromotive force between the reference substance and a bath contact which makes contact with the metal melt. The surface of the solid electrolyte is subjected to a surface cleaning treatment, primarily by means of etching.

52 Claims, 1 Drawing Sheet

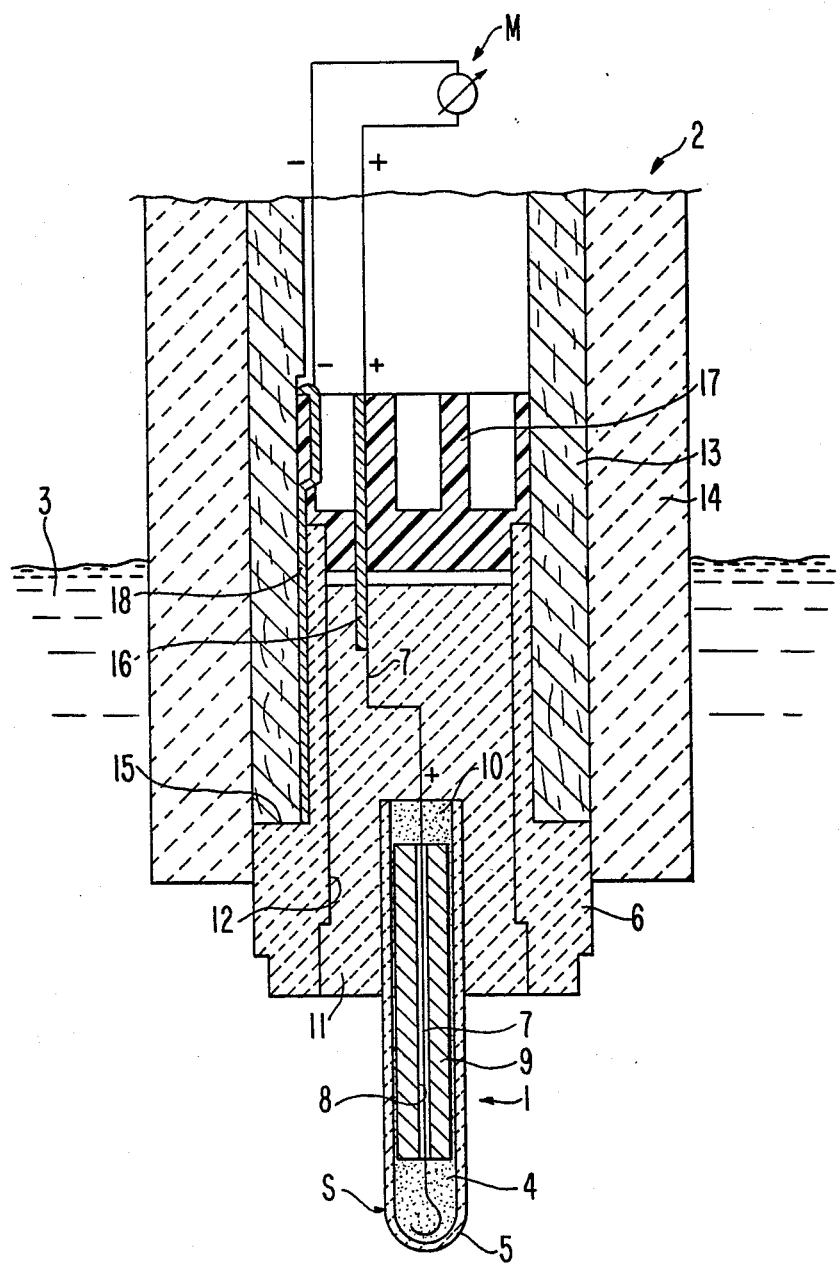

PROCESS FOR THE MANUFACTURE OF A MEASURING PROBE FOR A MEASURING HEAD TO DETECT THE OXYGEN ACTIVITY OF METAL MELTS AND A MEASURING PROBE MANUFACTURED BY SUCH A PROCESS

BACKGROUND OF THE INVENTION

The invention relates to the manufacture of a measuring probe for a measuring head to detect the oxygen activity of metal melts, in particular steel melts. The measuring probe has a reference substance of known oxygen activity and which, upon submersion into the metal melt, is separated from the metal melt by means of a refractory solid electrolyte that conducts electrons reliably and conducts primaarily oxygen at higher temperatures and which permits the measurement of the electromotive force between the reference substance and a bath contact making contact with the metal melt.

Such measuring heads are known from DE-OS 29 00 069 and DE-PS 33 45 540. In conducting the measurement of the partial pressure of oxygen of a metal melt, such a head is mounted at the end of a lance to be submerged into the melt. The manner in which the partial pressure of oxygen is measured with such a measuring head by means of the electromotive force between the measuring probe and a bath electrode is described for example in the journal "Steel and Iron", Vol. 95, (1975), issue 22, page 84. The measuring head used there is explained in detail in the brochure "FERROTRON, Oxygen probe for metallic melts" of Ferrotron Elektronik GmbH, Ratingen (Federal Republic of Germany), issue 1, 1982. In this case the measuring probe, designed as a $ZrO_2$ tube, can be provided with a coating that is inert with respect to the metal melt.

In order to improve the accuracy of measurement, in particular even in the case of aluminum-killed steels, attempts have been made to coat the measuring probe with platinum, but not with much success.

In is known from U.S. Pat. No. 4,135,012 how to etch the surface of ceramic products, manufactured on the basis of $ZrO_2$, with acid in order to attain a permanent adhesion of a metal coating. The acids that are use in this process are concentrated sulfuric acid, ammonium bisulfate, alkaline metal bisulfate and mixtures thereof, and are used at temperatures of at least 200° C.

According to U.S. Pat. No. 4,451,350, to improve the accuracy of measurement an attempt was made to provide the surface of the measuring probe with an aluminum layer containing a metal fluoride powder, whereby the wettability of the surface of the probe was to be increased. Yet this process, also, did not significantly improve the accuracy of measurement.

According to JP 62-157567 A (Token Sangyo), JP 60-177259 A (Sumitomo), JP 60-05763 A (Sumitomo), JP 56-100354 A (Hitachi), JP 56-100353 (Hitachi), JP 56-092450A and JP 84-044580 B (Hitachi), more or less good results were attained with surface coatings. However, the coating requires a relatively high cost of production, which increases the cost of the measuring probe. In addition, the surface coatings are susceptible to the attack of the metal melt so that their effectiveness is restricted.

SUMMARY OF THE INVENTION

The object of the invention is to provide a process for manufacturing a measuring probe for a measuring head employed to detect the oxygen activity of metal melts of the aforementioned type, in which process a measuring probe of higher efficiency, and thus the possibility of measuring the concentration of oxygen with greater accuracy, is attained.

This object is achieved according to the invention essentially by subjecting the surface of the solid electrolyte to a surface cleaning operation.

In this manner, there surprisingly is provided a measuring probe with which concentrations of oxygen ranging from 0 to 20 ppm can be measured with greater accuracy and with improved response time, compared to known probes.

The surface cleaning operation can be achieved, for example, by an etching process, a mechanical machining operation and/or blasting (sand blasting) operation. The etching process is the most effective and simplest.

In this connection, in accordance with another feature of the invention, it is proposed that, when conducting the surface cleaning operation, a surface layer ranging from 0.5 to 10 μm be removed from the solid electrolyte.

The etching process, according to the invention, is advantageously conducted by means of an acid, whereby hydrofluoric acid has proven to be especially beneficial. In this case the concentration of hydrofluoric acid ranges preferably from 0.5 to 50%. This etching process can be conducted, for example, at room temperature, whereby a suitable period of time ranges from approximately five to 60 minutes.

Following the etching process, the cleaned surface of the solid electrolyte should be washed with de-ionized water and, if necessary, a Hyamine solution and subsequently dried at high temperatures. Hyamine is a trade name of Rohm and Haas for a quarternary ammonium salt (benzethonium chloride).

Preferably, a material made essentially of $ZrO_2$ and containing preferably more than 95% by weight $ZrO_2$ should be used the solid electrolyte. MgO is suitable for stabilizing the $ZrO_2$. The solid electrolyte should contain approximately 3% by weight of MgO. Furthermore, the solid electrolyte should contain less than 1% by weight pyrogeneous silicic acid (SFH).

Especially good results in the manufacture of a measuring probe for high accuracy of measurement are obtained if the solid electrolyte contains approximately:

0.40–1.2% be weight $SiO_2$
max. 0.40% by weight CaO
2.0–3.5% by weight MgO
max. 0.40% by weight $Fe_2O_3$
max. 0.40% by weight $Al_2O_3$
max. 0.25% by weight $TiO_2$ With the framework of the invention the solid electrolyte should be manufactured as follows:
charging components,
mixing the components,
adding a binder,
grinding the mixture to a predetermined grain size,
drying the ground mixture,
pressing the ground mixture provided with a binder at a pressure of approximately 86 N/mm² (12,500 psi),
and burning the pressed substance at a temperature of approximately 1,785° C. (3,250° F.).

The invention also relates to a measuring probe which is manufactured according to the above described process.

BRIEF DESCRIPTION OF THE DRAWING

Other objects, features, advantages and applications of the present invention will be apparent from the following description of embodiments of the invention, with reference to the drawing, wherein all described and/or illustrated features form in themselves or in any arbitrary logical combination various aspects of the present invention, and wherein:

The single FIGURE is a sectional view of a measuring head to detect the oxygen activity of metal melts, including a measuring probe manufactured according to the invention, and submerged in a metal melt.

DETAILED DESCRIPTION OF THE INVENTION

A measuring probe 1 is a component of a measuring head 2, which is submerged into a metal melt 3 in order to detect the oxygen activity (partial pressure of oxygen) of the metal melt.

The measuring probe 1 includes a tube 5 having a closed end extending into the metal melt 3 and is made of a refractory solid electrolyte that conducts electrons reliably, but that conducts primarily oxygen at higher temperatures of the metal melt and that is based on $ZrO_2$ stabilized with MgO. The bottom region of the tube, as shown in the drawing, contains a powdery mixture comprising Cr and $Cr_2O_3$ as a reference substance 4 of known oxygen activity. The reference substance 4 is connected to an electrode or wire 7, made of molybdenum, which is guided upwardly but out of the tube through a central bore 8 of a supporting sleeve 9 mounted within the tube above the reference substance 4. The supporting sleeve 9 is held by a locking member 10 in the tube. The measuring probe 1 is embedded with its upper section in a refractory substance 11, for example a refractory cement, in the bottom section of the interior 12 of a bath contact 6 that is designed as a carrier sleeve and that is compression pressed and burned, for example, of a graphite-containing refractory substance, preferably on the basis of corundum, mullite, chamotte or the like, into its shape. Advantageous properties of the bath contact 6 follow in particular from DE-PS 33 45 540. The bath contact 6, designed as a carrier sleeve, extends with an upper reduced dimension end into a lance tube 13 made, for example, of cardboard and which is any case in the section projecting into the metal melt 3 is enclosed within a protective tube 14 made of refractory material. In this case the bottom section of the supporting tube 14 projects above a separating line 15 between the downward pointing face of the lance tube 13 and a shoulder of the bath contact 6 provided at this point. The wire 7 made of molybdenum is connected to a connection contact 16 of a connection support 17 made of non-conducting material such as plastic. The bath contact designed as a carrier sleeve is also provided externally with a connection contact 18, which is guided into the connection support 17 so that a measuring connection can be made between a plug (not illustrated) and a measuring device M to measure the electromotive force between the reference substance 4 and the bath contact 6, and thus the oxygen activity (partial pressure of oxygen) of the metal melt into which the measuring head 2 is submerged.

The surface S of the probe structure formed by the solid electrolyte in the shape of tube 5 closed at the bottom end thereof is cleaned according to the invention by means of a surface cleaning treatment, for example, in an etching process by means of 0.5 to 50% hydrofluoric acid. In this case photographic examinations have shown that non-treated solid electrolyte has a relatively smooth structure, whereas following etching the tetragonal phase of the surface of $ZrO_2$ showed clearly. This results in the surprising effect of increased accuracy of measurement, down to a range of 0 to 20 ppm of oxygen concentration, with the measuring probe 1 prepared in accordance with the invention, with improved response time.

The best accuracy of measuring was attained with a solid electrolyte which contained more than 95% by weight of $ZrO_2$, approximately 3% by weight of MgO, and approximately 0.5% by weight of $SiO_2$.

According to the preferred analysis, the solid electrolyte contained:

0.40–1.2% be weight $SiO_2$
max. 0.40% by weight CaO
2.0–3.5% by weight MgO
max. 0.40% by weight $Fe_2O_3$
max. 0.40% by weight $Al_2O_3$
max. 0.25% by weight $TiO_2$ The etching processes of the invention were conducted, with positive test results of an improved accuracy of measurement, as follows:

Use of an etching solution of 49% HF in a beaker-shaped vessel, which was mounted in a ceramic crucible and this in turn was mounted in a water tank. The etching period lasted 10 minutes. After the hydrofluoric acid was poured off, the etched surface of the tubular solid electrolyte was rinsed three times with de-ionized water, than twice with Hyamine solution and finally twice again with de-ionized water. The outer surface of the tubular solid electrolyte was subsequently dried with a cloth and the interior of the tube was cleaned with a pipe cleaner. Then the thus etched solid electrolyte tube 5 was dried in a heated furnace at 160° C. for 10 minutes.

EXAMPLE

To manufacture measuring probes (sensors) from partially stabilized zirconium oxide, monoclinic zirconium oxide containing less than 0.25% $SiO_2$ and having a grain size below 10 μm was used. A mixture was prepared from 95.25% by weight of zirconium oxide, 3.1% by weight of powdery magnesium hydroxide and 0.65% by weight of pyrogeneous silicon dioxide having a grain size 70% below 5 μm. While adding 0.6% by weight of sodium polymethacrylacrylate (sodium polymethacrylate) as dispersing agent, 3.3% by weight polyvinyl alcohol resin and water, the mixture was processed to a ceramic suspension. The ceramic suspension was ground in the conventional manner with a vibrating mill until the average grain size ranged from 2 to 3 μm (measured as the average grain size based on volume according to a laser light beam diffraction process). Then compression moldable granules were prepared by means of flash drying from the ceramic suspension (ceramic slip). Measuring probes were manufactured by means of an isostatic pressing process (dry bag isostatic pressing) from the granules. Such probes were burned at 1,785° C. for two hours.

Solid measuring probes made of partially stabilized zirconium dioxide with approximately 50% monoclinic zirconium dioxide were obtained. The chemical analysis of the burned measuring probes yielded, besides $ZrO_2$, according to atomic absorption analysis:

| MgO | 2.98% by weight |
| --- | --- |
| SiO$_2$ | 0.65% by weight |
| CaO | 0.24% by weight |
| Al$_2$O$_3$ | 0.10% by weight |
| Fe$_2$O$_3$ | 0.07% by weight |
| TiO$_2$ | 0.05% by weight |

The surfaces of the measuring probes were treated and activated by etching with acid. A 49% concentration of HF was added over a period of 10 minutes. During this time the measuring probes were moved by means of agitation or rolling at ambient temperature with the etching solution in a plastic vessel. The surfaces of the measuring probes also can be treated with a smaller concentration of HF, e.g. 2% concentration of HF, over a period of 40 minutes.

After treating the surfaces of the measuring probes by means of etching, the measuring probes were removed from the etching liquid and cleaned five times with de-ionized water, rinsed, and dried. The reduction in the wall thickness of the measuring probes was determined computationally from the loss of weight of the measuring probes due to etching, the surface area and the specific weight of the measuring probes. Following etching with 49% HF, a reduction of 5.8 $\mu$m in wall thickness was found.

Upon application to measure the concentraation of oxygen in an aluminum-killed steel melt at temperatures ranging from 1,540° to 1,620° C., the measuring probes, surface-treated according to the above example, resulted in faultless measurements in the range of 0 to 20 ppm with simultaneously shorter response time.

We claim:

1. In a process for the manufacture of a measuring probe for use in a measuring head to detect the oxygen activity of a metal melt, particularly a steel melt, and wherein said measuring probe is intended to be immersed in the metal melt, said process including providing a probe structure having a surface to contact the metal melt and formed of a solid refractory electrolyte material having the properties of conducting electrons reliably and conducting primarily oxygen at temperatures of the metal melt, the improvement comprising:
    finishing said manufacture by subjecting said surface to a mechanical cleaning treatment comprising a blasting operation; and
    thereafter maintaining the thus treated surface free and uncovered so that it may directly contact the metal melt during use;
    thereby imparting to the thus finished measuring probe the properties of improved accuracy and efficiency of measurement.

2. The improvement claimed in claim 1, wherein said blasting operation comprises sand blasting.

3. The improvement claimed in claim 1, wherein said solid refractory electrolyte material comprises primarily ZrO$_2$.

4. The improvement claimed in claim 3, wherein said material comprises more than 95% by weight ZrO$_2$.

5. The improvement claimed in claim 4, wherein said material further comprises approximately 3% by weight MgO.

6. The improvement claimed in claim 4, wherein said material comprises less than 1% by weight of pyrogeneous silicic acid.

7. The improvement claimed in claim 4, wherein said material comprises approximately:
    0.40-1.2% be weight SiO$_2$
    max. 0.40% by weight CaO
    2.0-3.5% by weight MgO
    max. 0.40% by weight Fe$_2$O$_3$
    max. 0.40% by weight Al$_2$O$_3$
    max. 0.25% by weight TiO$_2$.

8. The improvement claimed in claim 1, wherein said providing comprises forming said probe structure by a sequence of operations including:
    charging the components of said material,
    mixing said components,
    adding a binder,
    grinding the resultant mixture to a predetermined grain size,
    drying the thus ground mixture,
    pressing said ground mixture including said binder at a pressure of approximately 86 N/mm$^2$ (12,500 psi), and
    burning the thus pressed structure at a temperature of approximately 1,785° C. (3,250° F.).

9. The improvement claimed in claim 1, wherein said providing comprises forming said probe structure as a hollow tube having a closed end to be immersed in the metal melt and an outer surface forming said surface subjected to said cleaning treatment.

10. A measuring probe for use in a measuring head to detect the oxygen activity of a metal melt, particularly a steel melt, and intended to be immersed in the metal melt, said probe comprising:
    a probe structure having a surface to contact the metal melt and formed of a solid refractory electrolyte material having the properties of conducting electrons reliably and conducting primarily oxygen at temperatures of the metal melt; and
    said surface having a configuration resulting from a mechanical cleaning treatment thereof by a blasting operation and being free and uncovered so that it may directly contact the metal during use.

11. A probe as claimed in claim 10, wherein said blasting operation comprises sand blasting.

12. A probe as claimed in claim 10, wherein said solid refractory electrolyte material comprises primarily ZrO$_2$.

13. A probe as claimed in claim 10, wherein said material comprises more than 95% by weight ZrO$_2$.

14. A probe as claimed in claim 13, wherein said material comprises less than 1% by weight of pyrogeneous silicic acid.

15. A probe as claimed in claim 13, wherein said material comprises approximately:
    0.40-1.2% be weight SiO$_2$
    max. 0.40% by weight CaO
    2.0-3.5% by weight MgO
    max. 0.40% by weight Fe$_2$O$_3$
    max. 0.40% by weight Al$_2$O$_3$
    max. 0.25% by weight TiO$_2$.

16. A probe as claimed in claim 13, wherein said material further comprises approximately 3% by weight MgO.

17. A probe as claimed in claim 10, having a tubular shape with a closed end to be immersed in the metal melt and an outer surface forming said surface subjected to said cleaning treatment.

18. A probe as claimed in claim 17, further comprising a reference substance of known oxygen activity within said closed end of said tubular shape and to be separated, during use of said probe, from the metal melt by said material of said probe.

19. A probe as claimed in claim 18, further comprising an electrode in contact with said reference substance and extending outwardly of said tubular shape.

20. In a process for the manufacture of a measuring probe for use in a measuring head to detect the oxygen activity of a metal melt, particularly a steel melt, and wherein said measuring probe is intended to be immersed in the metal melt, said process including providing a probe structure having a surface to contact the metal melt and formed of a solid refractory electrolyte material having the properties of conducting electrons reliably and conducting primarily oxygen at temperatures of the metal melt, the improvement comprising:
  finishing said manufacture by subjecting said surface to a mechanical cleaning treatment during which a surface layer of approximately 0.2 to 10 μm of said solid refractory electrolyte material is removed; and
  thereafter maintaining the thus treated surface free and uncovered so that it may directly contact the metal melt during use;
  thereby imparting to the thus finished measuring probe the properties of improved accuracy and efficiency of measurement.

21. The improvement claimed in claim 20, wherein said solid refractory electrolyte material comprises primarily $ZrO_2$.

22. The improvement claimed in claim 21, wherein said material comprises more than 95% by weight $ZrO_2$.

23. The improvement claimed in claim 22, wherein said material further comprises approximately 3% by weight MgO.

24. The improvement claimed in claim 22, wherein said material comprises less than 1% by weight of pyrogeneous silicic acid.

25. The improvement claimed in claim 22, wherein said material comprises approximately:
  0.40–1.2% be weight $SiO_2$
  max. 0.40% by weight CaO
  2.0–3.5% by weight MgO
  max. 0.40% by weight $Fe_2O_3$
  max. 0.40% by weight $Al_2O_3$
  max. 0.25% by weight $TiO_2$.

26. The improvement claimed in claim 20, wherein said providing comprises forming said probe structure by a sequence of operations including:
  charging the components of said material,
  mixing said components,
  adding a binder,
  grinding the resultant mixture to a predetermined grain size,
  drying the thus ground mixture,
  pressing said ground mixture including said binder at a pressure of approximately 86 N/mm² (12,500 psi), and
  burning the thus pressed structure at a temperature of approximately 1,785° C. (3,250° F.).

27. The improvement claimed in claim 20, wherein said providing comprises forming said probe structure as a hollow tube having a closed end to be immersed in the metal melt and an outer surface forming said surface subjected to said cleaning treatment.

28. In a process for the manufacture of a measuring probe for use in a measuring head to detect the oxygen activity of a metal melt, particularly a steel melt, and wherein said measuring probe is intended to be immersed in the metal melt, said process including providing a probe structure having a surface to contact the metal melt and formed of a solid refractory electrolyte material having the properties of conducting electrons reliably and conducting primarily oxygen at temperatures of the metal melt, the improvement comprising:
  finishing said manufacture by subjecting said surface to a cleaning treatment comprising an etching operation; and
  thereafter maintaining the thus treated surface free and uncovered so that it may directly contact the metal melt during use;
  thereby imparting to the thus finished measuring probe the properties of improved accuracy and efficiency of measurement.

29. The improvement claimed in claim 28, wherein during said etching treatment a surface layer of approximately 0.2 to 10 μm of said solid refractory electrolyte material is removed.

30. The improvement claimed in claim 28, wherein said etching treatment comprises an acid etching operation.

31. The improvement claimed in claim 30, wherein hydrofluoric acid is used in said acid etching operation.

32. The improvement claimed in claim 31, wherein said hydrofluoric acid is used in a concentration of from 0.5 to 50%.

33. The improvement claimed in claim 32, wherein said acid etching operation is conducted for a time period of approximately from five to sixty minutes.

34. The improvement claimed in claim 31, wherein said acid etching operation is conducted at room temperature.

35. The improvement claimed in claim 30, wherein said surface cleaning treatment further comprises, after said acid etching operation, washing with de-ionized water and drying at a temperature above room temperature.

36. The improvement claimed in claim 28, wherein said solid refractory electrolyte material comprises primarily $ZrO_2$.

37. The improvement claimed in claim 36, wherein said material comprises more than 95% by weight $ZrO_2$.

38. The improvement claimed in claim 37, wherein said material further comprises approximately 3% by weight MgO.

39. The improvement claimed in claim 37, wherein said material comprises less than 1% by weight of pyrogeneous silicic acid.

40. The improvement claimed in claim 37, wherein said material comprises approximately:
  0.40–1.2% be weight $SiO_2$
  max. 0.40% by weight CaO
  2.0–3.5% by weight MgO
  max. 0.40% by weight $Fe_2O_3$
  max. 0.40% by weight $Al_2O_3$
  max. 0.25% by weight $TiO_2$.

41. The improvement claimed in claim 28, wherein said providing comprises forming said probe structure by a sequence of operations including:
  charging the components of said material,
  mixing said components,
  adding a binder,
  grinding the resultant mixture to a predetermined grain size, drying the thus ground mixture, pressing said ground mixture including said binder at a pressure of approximately 86 N/mm² (12,500 psi), and burning the thus pressed structure at a temperature of approximately 1,785° C. (3,250° F.).

42. The improvement claimed in claim 28, wherein said providing comprises forming said probe structure as a hollow tube having a closed end to be immersed in the metal melt and an outer surface forming said surface subjected to said cleaning treatment.

43. A measuring probe for use in a measuring head to detect the oxygen activity of a metal melt, particularly a steel melt, and intended to be immersed in the metal melt, said probe comprising:

a probe structure having a surface to contact the metal melt and formed of a solid refractory electrolyte material having the properties of conducting electrons reliably and conducting primarily oxygen at temperatures of the metal melt; and said surface having a configuration resulting from a cleaning treatment thereof by an etching operation and being free and uncovered so that it may directly contact the metal during use.

44. A probe as claimed in claim 43, wherein said etching treatment comprises an acid etching operation.

45. A probe as claimed in claim 43, wherein said solid refractory electrolyte material comprises primarily $ZrO_2$.

46. A probe as claimed in claim 43, wherein said material comprises more than 95% by weight $ZrO_2$.

47. A probe as claimed in claim 46, wherein said material further comprises approximately 3% by weight MgO.

48. A probe as claimed in claim 46, wherein said material comprises less than 1% by weight of pyrogeneous silicic acid.

49. A probe as claimed in claim 46, wherein said material comprises approximately:

0.40–1.2% be weight $SiO_2$ max. 0.40% by weight CaO 2.0–3.5% by weight MgO max. 0.40% by weight $Fe_2O_3$ max. 0.40% by weight $Al_2O_3$ max. 0.25% by weight $TiO_2$.

50. A probe as claimed in claim 43, having a tubular shape with a closed end to be immersed in the metal melt and an outer surface forming said surface subjected to said cleaning treatment.

51. A probe as claimed in claim 50, further comprising a reference substance of known oxygen activity within said closed end of said tubular shape and to be separated, during use of said probe, from the metal melt by said material of said probe.

52. A probe as claimed in claim 51, further comprising an electrode in contact with said reference substance and extending outwardly of said tubular shape.

* * * * *